United States Patent [19]
Menard et al.

[11] Patent Number: 5,108,928
[45] Date of Patent: Apr. 28, 1992

[54] METHOD AND APPARATUS FOR DELIVERING A SAMPLE TO MULTIPLE ANALYTICAL INSTRUMENTS

[75] Inventors: Kevin P. Menard, Euless; H. Randy O'Neal, Weatherford, both of Tex.

[73] Assignee: General Dynamics Corporation, Fort Worth, Tex.

[21] Appl. No.: 434,330

[22] Filed: Nov. 13, 1989

[51] Int. Cl.$^5$ .................. G01N 1/18; G01N 35/08
[52] U.S. Cl. .................... 436/43; 436/53; 422/681; 422/81; 422/82
[58] Field of Search .................. 436/52, 53, 43; 422/68.1, 70, 81, 82, 93, 62

[56] References Cited

U.S. PATENT DOCUMENTS

| | | |
|---|---|---|
| 2,837,920 | 6/1958 | Keith . |
| 3,030,192 | 5/1958 | Schneider, Jr. . |
| 3,259,462 | 8/1962 | Anscherlik . |
| 3,764,268 | 11/1973 | Kosowsky et al. .................. 422/82 |
| 4,049,381 | 10/1977 | Burn et al. .................. 422/82 |
| 4,403,503 | 10/1983 | Banerjee et al. .................. 422/70 |
| 4,520,108 | 5/1985 | Yoshida et al. .................. 436/52 |
| 4,577,492 | 3/1986 | Holba et al. .................. 422/70 |
| 4,592,842 | 6/1986 | Tomlinson .................. 422/70 |
| 4,645,647 | 2/1987 | Yoshida et al. .................. 422/81 |
| 4,680,270 | 7/1987 | Mitsumaki et al. .................. 436/52 |
| 4,704,256 | 11/1987 | Hood et al. . |
| 4,718,280 | 1/1988 | Leschonski et al. . |
| 4,865,811 | 10/1989 | Newton et al. .................. 436/52 |

Primary Examiner—David L. Lacey
Assistant Examiner—David Redding
Attorney, Agent, or Firm—James E. Bradley

[57] ABSTRACT

A method and equipment for making a chemical analysis of a sample enables multiple analyses to be conducted simultaneously. The system includes a number of injection valves connected in series to a sample inlet line. Each injection valve is connected in a parallel to a separate detection unit. Each injection valve is connected to a pressurized source such as a solvent pump. This equipment includes a sample preparation unit which injects the sample to flow through each of the valves. Each of the valves will retain a portion of the sample in a sample chamber. Each valve will rotate to an injecting position wherein the pressurized solvent pushes the sample into the separate detection units.

10 Claims, 2 Drawing Sheets

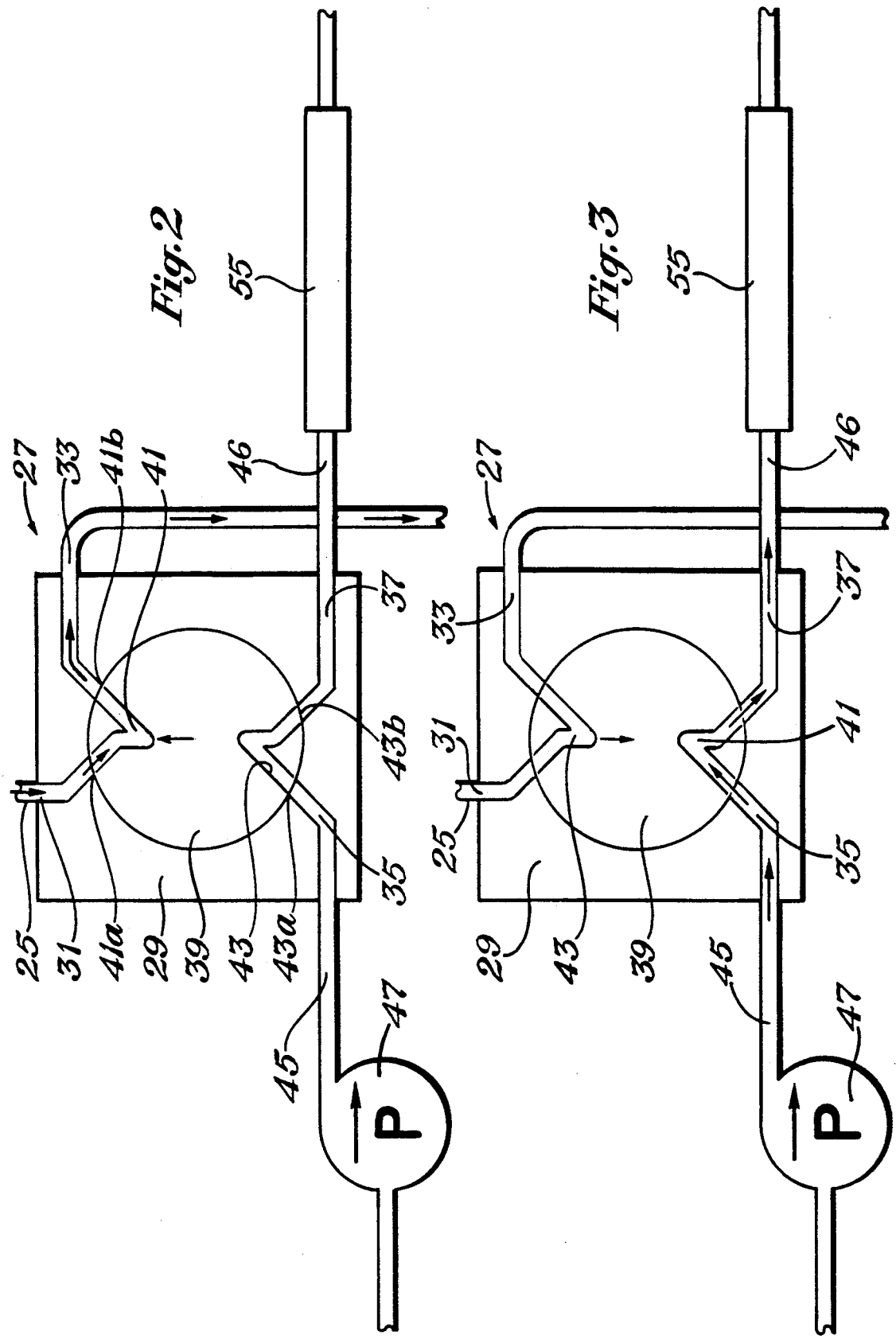

METHOD AND APPARATUS FOR DELIVERING A SAMPLE TO MULTIPLE ANALYTICAL INSTRUMENTS

This invention was made with Government support under Contract No. F33657-84-C-0247 awarded by Department of the Air Force. The Government has certain rights in this invention.

BACKGROUND OF THE INVENTION

1. Field of the Invention

This invention relates in general to equipment and methods for chemically analyzing liquid samples, and in particular to equipment and a method for delivering a sample simultaneously to a number of different analytical instruments.

2. Description of the Prior Art

In many industries, various tests must be performed on liquid samples. For example, certain components of military aircraft are made of composite fiber layers. The resins within these composites must be tested for quality assurance. The samples will be prepared in solvents. These samples are then injected into various detecting equipment such as high performance liquid chromatographs (HPLC), size exclusion chromatographs (SEC), gel permeation chromatographs (GPC), and moisture analyzers. Normally individual samples will be prepared and injected separately into each instrument. Quality assurance requirements often dictate that duplicate tests be run.

A disadvantage of this prior technique is that it takes a considerable amount of time to prepare a sample. Even if the sample is prepared by a robotic device, several hours can be required to prepare the sample. After preparation, running the HPLC test itself can take one-half hour or more. Consequently, if numerous samples have to be tested frequently, considerable expense will be involved in labor and equipment to meet the demand.

Proposals have been suggested to split the sample as it is injected into the sample inlet tube. The sample would then run through separate detecting instruments. A disadvantage of this proposal is that splitting of a sample could cause variations in the flow rate. This could cause errors in the analysis. Also, it would require that all analyses use the same solvent system. This would block the use of GPC and HPLC chromatographs at the same time, because these chromatographs often require different types of solvents.

In the detections systems used in the past, injection valves are used. These injection valves have a spool within them that contains a sample chamber and a solvent chamber. Each chamber has an inlet and an outlet. The injection valve has a sample inlet port, a sample excess port, a solvent inlet port and a solvent/sample outlet port. When operating these injection valves, first the sample is injected in through the sample inlet port to flow through the sample chamber and out the sample excess outlet port. A portion of the sample will remain in the sample chamber. Then, the spool rotates to align the sample chamber inlets and outlets with the solvent inlet and solvent/sample outlet ports, respectively. A solvent pump will then push the sample on to the detection units. While this is a workable technique, heretofore it has only been used with a single detection unit

SUMMARY OF THE INVENTION

In this invention, a plurality of injection valves are connected in series to a single sample inlet line. Each injection valve is also connected in parallel with its own solvent line and with a separate detection unit. The solvent line leads from a separate source of solvent under pressure to a separate detection unit.

The sample will be injected into the sample line. It will flow sequentially through each injection valve with a portion remaining in the sample chamber within the spool of each injection valve. Then, the spool will be rotated for each injection valve from the receiving position to an injecting position. In this position, the sample chamber of each injection valve will register with the inlet to the solvent line. The outlet of each sample chamber will register with a line leading to one of the detection units. The pumps will simultaneously push the samples into the various detection units.

BRIEF DESCRIPTION OF THE DRAWINGS

FIG. 2 is an enlarged schematic view illustrating one of the injection valves used with the system of FIG. 1 and shown in a receiving position.

FIG. 3 is an enlarged schematic view of the injection valve of FIG. 2, and shown in an injecting position.

DETAILED DESCRIPTION OF THE INVENTION

Figure 1:
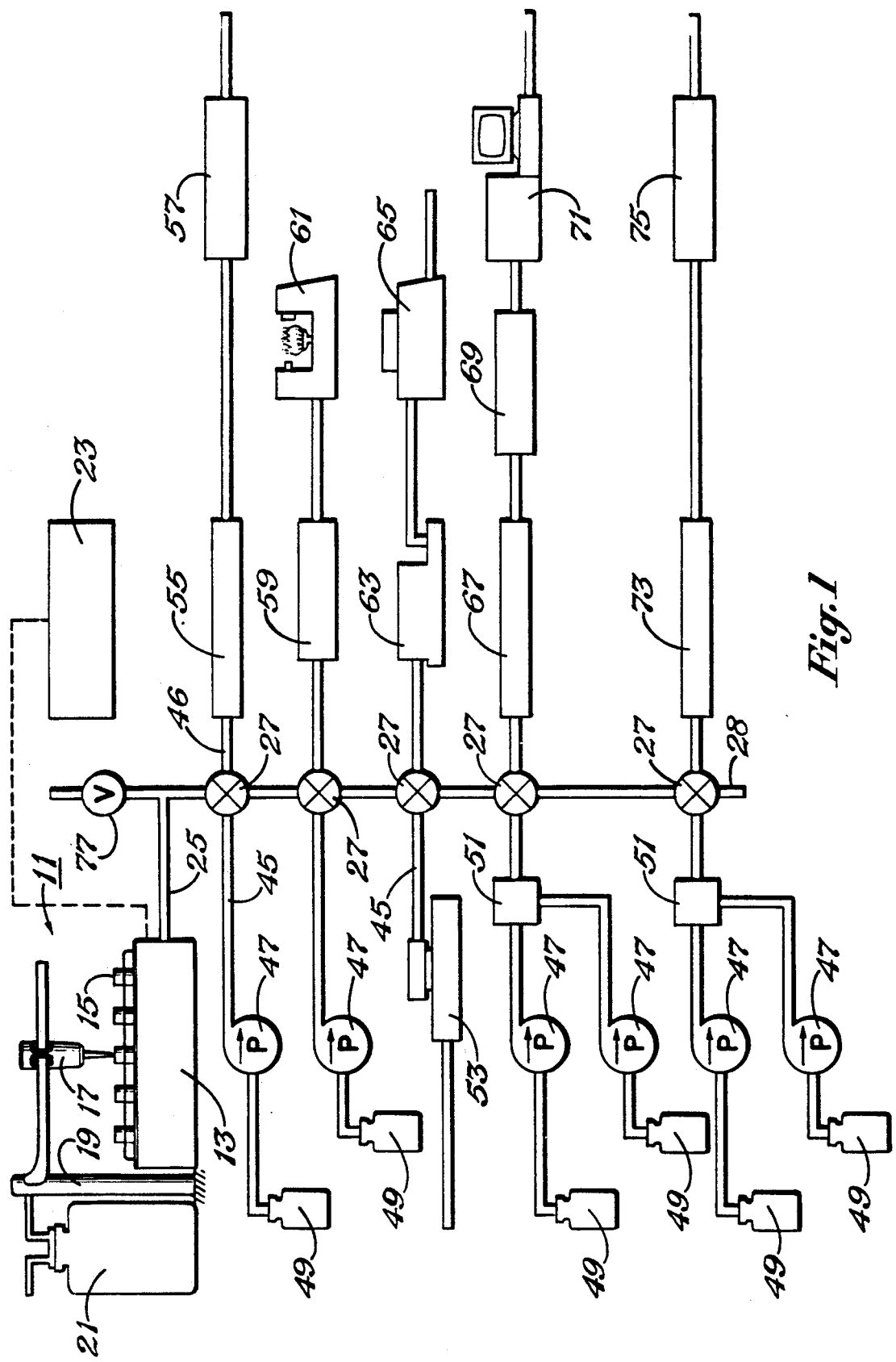
FIG. 1 is a schematic representation of an apparatus for testing multiple sample portions according to this invention.

Referring to FIG. 1, the system of this invention preferably includes a robotic sample preparation unit 11. Unit 11 is conventional and may be purchased from various sources. It will include a base 13 which holds a number of sample tubes 15. A probe 17 travels on an arm 19 to distribute fluids into the tube 15 and otherwise prepare the samples. The probe 17 will be connected to a solvent tank 21. A computer 23 will operate the unit 11 to prepare the sample. Preparing a sample may take up to about four hours.

Once prepared, the robotic sample preparation unit 11 will inject the sample into a sample inlet line 25. A number of injection valves 27 will be connected in series in the sample inlet line 25. In the embodiment shown, five injection valves 27 are connected together in the sample inlet line 25. The sample injected into line 25 will be delivered to each of the injection valves 27, with any excess passing out a conduit 28 to a waste container (now shown).

Referring to FIGS. 2 and 3, the injection valves 27 are conventional and may be purchased from various sources. Each injection valve 27 has a housing 29. The housing 29 has four ports which are as follows: sample inlet port 31; excess sample outlet port 33, solvent inlet port 35; and solvent/sample outlet port 37. Also, each injection valve 27 has a selection means comprising a rotatable spool 39 contained within it.

Spool 39 contains a sample chamber 41 and a solvent chamber 43. Each chamber 41, 43 is a triangular passage, preferably spaced 180 degrees apart from the other. The sample chamber 41 has an inlet 41a and an outlet 41b. In the receiving or loading position as shown in FIG. 2, the inlet 41a will align with the sample inlet port 31, which connects the inlet 41a with the sample inlet line 25 in an upstream direction. The outlet 41b will align with the excess sample outlet port 33, which connects the outlet 41b with the sample inlet line 25 in a downstream direction. The triangular configuration of the sample chamber 41 enables it to serve as a retaining means to retain a portion of the sample fluid being conveyed through the sample inlet port 31, after discontinuance of the transmission of the sample.

Similarly, the solvent chamber 43 has an inlet 43a and an outlet 43b. The inlet 43a aligns with the solvent inlet port 35 in the position in FIG. 2. The outlet 43b aligns with the solvent/sample outlet port 37 in the position shown in FIG. 2.

Referring to FIG. 3, the spool 39 includes an electrical means which when actuated will rotate the spool 39 from the loading position shown in FIG. 2 to the injecting position shown in FIG. 3. The extent of the rotation is 180 degrees. The sample chamber 41 will then align with the solvent inlet port 35 and with the solvent/sample outlet port 37. The solvent chamber 43 will align with the sample inlet port 31 and excess sample outlet port 33.

Referring again to FIG. 1, each injection valve 27 will be connected to a separate solvent line 45. Also, the solvent line 45 continues on the opposite side of the injection valve 27, this portion being referred to herein as a detection unit line 46. A separate detection unit line 46 exists for each of the injection valves 27. The solvent inlet port 35 connects to the solvent line 45 in an upstream direction. The solvent/sample outlet port 37 connects with the detection unit line 46 in a downstream direction.

In the embodiment shown, all but one of the solvent lines 45 will be connected to one or more pumps 47. Each pump 47 pumps solvent from a tank 49. The solvents may be different for the various injection valves 27. The lowermost two solvent lines 45, as shown in FIG. 1, connect to two separate pumps 47, each of which leads to a mixing chamber 51. Two different solvents will be supplied to the mixing chamber 51, where they mix and flow to the injection valve 27. One of the solvent lines 45 will be connected to a compressed gas system 53 for supplying compressed gas to the injection valve 27.

The uppermost detection unit line 46, as shown in FIG. 1, connects to a column 55, which may be either a size exclusion chromatograph (SEC) or a gel permeation chromatograph (GPC). This chromatograph is a conventional instrument which separates the sample by molecular size. The output from the column 55 leads to a detector 57 of conventional nature. The detector uses ultraviolet light to detect the separated molecules as they flow through.

The second injection valve 27 may be connected to different detection units. The unit shown in the drawing can be a sample pretreater or filter 59 which leads to an atomic absorption spectrometer 61. The spectrometer 61 burns the sample, making an analysis in a conventional manner.

The third injection valve 27 is shown to be connected to the compressed gas system 53. This valve 27 will be connected to a detection unit that comprises a moisture analyzer 65. A sample loader 63 supplies the sample to the moisture analyzer 65.

A high performance (or pressure) liquid chromatograph (HPLC) column 67 will connect to the fourth injection valve 27. The HPLC column 67 sorts the sample by chemical affinity. Its output connects to a conventional detector 69. In addition, the sample from the detector 69 may be supplied to a mass spectrometer 71 to determine the atomic weights of the constituents found in the sample.

For the purpose of duplication of the sample, another HPLC column 73 and detector 75 will be connected to the last injection valve 27. There will be no need to analyze a duplicate sample with a mass spectrometer 71.

The system also has a manual valve 77 which may be used to inject a sample manually rather than the robotic sample preparation unit 11. In operation the sample preparation unit 11 will prepare a sample that will have a volume in the range from 5 to 100 times the volume of all of the sample chambers 41 (FIG. 2). The injection valves 27 will be in the loading position shown in FIG. 2. The pumps 47 may be pumping solvent through the ports 35, 37 and solvent chambers 43 to maintain the system flushed. Then the sample will be injected into the sample inlet line 25. It will flow into the sample inlet port 31 of the first injection valve 27. It flows into the sample chamber 41. A portion flows out the excess sample outlet port 33, and a portion remains in the sample chamber 41.

From the excess sample outlet port 33, the remaining portion of the sample flows into the sample inlet port 31 of the next injection valve 27. The sample will thus flow in series through each of the injection valves 27. The excess sample will flow out the outlet conduit 28 to waste. A portion of the sample remains in each sample chamber 41.

Once each sample chamber 41 has been filled, the operator actuates the injection valves 27 to rotate to the injecting position shown in FIG. 3. Preferably, the injection valves 27 are electrically connected to a single switch, so that they may be rotated simultaneously. In this position, each of the sample chambers 41 will be aligned with a solvent inlet port 35 and a solvent/sample outlet port 37.

The pumps 47 supply solvent under pressure to push the samples from the sample chambers 41 into the detection unit lines 46. The samples proceed through the various detection units shown in FIG. 1. This includes units 55, 59, 67 and 73. In the case of the injection valve 27 which is connected to the compressed gas system 53, compressed gas will push the sample to sample loader 63. The pumps 47 and the injection valves 27 will remain in the injecting position until the sample is fully analyzed by the various detection units.

The invention has significant advantages. Connecting the injection valves in series to a sample preparation unit, and connecting each valve in parallel to a separate detection unit enables multiple analyses to be run simultaneously on a single prepared sample. This greatly saves time and expense.

While the invention has been shown in only one of its forms, it should be apparent to those skilled in the art that it is not so limited, but is susceptible to various changes without departing from the scope of the invention.

We claim:

1. An apparatus for distributing a sample to multiple detection units, comprising in combination:
   a sample inlet line;
   a plurality of solvent lines, each constructed so as to be connected in parallel with each other and in flow communication with a separate one of the detection units;
   a plurality of injection valves, each separately connected in flow communication into each one of said plurality of solvent lines and also connected in series in the sample inlet line, each one of said plurality of injection valves comprising a sample inlet port, an excess sample outlet port, a solvent inlet port and solvent/sample outlet port, the sample inlet port positioned and arranged in flow communication with the sample inlet line, the excess sample outlet port positioned and arranged in flow communication with the sample inlet line which is in flow communication with one of said plurality of injection valves in series, the solvent inlet port positioned and arranged in flow communication with one of said plurality of solvent lines, the solvent/sample outlet port positioned and arranged in flow communication with one of said plurality of solvent lines which is in flow communication with one of said detection units;

means for injecting a sample into the sample inlet line for conveying the sample through each of the sample inlet ports and excess sample outlet ports of each one of said plurality of injection valves;

retaining means in each one of said plurality of injection valves, constructed so as to be in a receiving position in which the retaining means is in flow communication with the sample inlet port and excess sample outlet port so as to receive and retain a sample portion of the sample as the sample flow through the sample inlet port out the excess sample outlet port;

selection means for selectively positioning the retaining means from the receiving position to an injection position such that said retaining means is in flow communication with the solvent inlet and solvent/sample outlet ports; and pressure means for applying a fluid under pressure to each of the solvent lines of each one of said plurality of injection valves to push each of the sample portions from the retaining means out the solvent/sample outlet port and into one of the detection units.

2. The apparatus according to claim 1 wherein the pressure means comprises a tank constructed so as to hold the solvent and a separate pump for at least two of said plurality solvent lines for pumping the solvent through the solvent line.

3. The apparatus according to claim 1 wherein the means for injecting a sample into the sample inlet line comprises a robotic sample preparation unit.

4. The apparatus according to claim 1 wherein the selection means comprises a selectively rotatable spool located in each one of said plurality of injection valves, and the retaining means comprises a sample chamber in the spool having an inlet and an outlet which are in flow communication with the sample inlet port and excess sample outlet port, respectively, in the receiving position and with the solvent inlet port and solvent/sample outlet port, respectively, when the spool rotates to the injecting position.

5. The apparatus according to claim 4 further comprising a solvent chamber in the spool having an inlet and an outlet which are in flow communication with the solvent inlet port and solvent/sample outlet port, respectively, when the spool is in the receiving position.

6. An apparatus for chemically analyzing a sample, comprising in combination;
 a sample inlet line;
 a plurality of solvent lines, each in parallel with each other;

a plurality of detection units, each connected in flow communication with at least one of said plurality of said solvent lines;

a plurality of injection valves, each connected in flow communication with at least one of said plurality of said solvent lines, each also connected in series with the sample inlet line, each one of said plurality of injection valves comprising a sample inlet port, an excess sample outlet port, a solvent inlet port and solvent/sample outlet port, the sample inlet port positioned and arranged in flow communication with the sample inlet line, the excess sample outlet port positioned and arranged in flow communication with the sample inlet line which is in flow communication with one of said plurality of injection valves n series, the solvent inlet port positioned and arranged in flow communication with one of said plurality of solvent lines, the solvent/sample outlet port positioned and arranged in flow communication with one of said plurality of solvent lines which is in flow communication with one of said plurality of detection units;

means for preparing a sample and injecting the sample into the sample inlet line so as to convey the sample through each of the sample inlet ports and excess sample outlet ports of each one of said plurality of injection valves;

a selectively rotatable spool located in each one of said plurality of injection valves and constructed so as to be moved between a receiving position and an injecting position;

a sample chamber in each of the spools constructed so as to have an inlet and an outlet which is in flow communication with the sample inlet port and excess sample outlet port, respectively, in the receiving position to receive and retain a sample portion and with the solvent inlet port and solvent/sample outlet port, respectively, when the spool rotates to the injecting position; and pressure means for applying a fluid under pressure to each one of said plurality of solvent lines of each one of said plurality of injection valves to push each of the sample portions from the sample chambers out the solvent/sample outlet port and into a separate one of said plurality of detection units when the spool is in the injecting position.

7. The apparatus according to claim 6 further comprising a solvent chamber in the spool having an inlet and an outlet which are in flow communication with the solvent inlet port and solvent/sample outlet port, respectively, when the spool is in the receiving position.

8. An method for distributing a sample to multiple detection units, comprising in combination:
 providing a plurality of injection valves each which comprise a sample chamber, a sample inlet port, an excess sample outlet port, a solvent inlet port, a solvent/sample outlet port and means for selectively connecting in flow communication with the sample chamber with the sample inlet port and excess sample outlet port while in a receiving position, and with the solvent inlet port and solvent/sample outlet port when in an injecting position;
 connecting each one of said plurality of injection valves in series in a sample inlet line by connecting each sample inlet port to the sample inlet line, and by connecting each excess sample outlet port to the sample inlet line;

connecting each solvent/sample outlet port of each one of said plurality of injection valves in parallel to a separate detection unit;

injecting a sample into the sample inlet line so as to convey the sample through each of the sample inlet ports and excess sample outlet ports of each one of said plurality of the injection valves while each one of said plurality of the injection valves are in the receiving positions;

retaining in each of the sample chambers a sample portion of the sample as the sample flows through the sample inlet port out the excess sample outlet port;

moving the sample chambers to the injecting position in flow communication with the solvent inlet and solvent/sample outlet ports; and applying a fluid under pressure to the solvent inlet port of each one of said plurality of the injection valves while the sample chambers are in the injecting positions, thereby pushing each of the sample portions from the sample chambers out the solvent/sample outlet ports and into each of the detection units.

9. The method according to claim 8 wherein the sample chambers are moved to the injecting position simultaneously, and wherein the fluid under pressure is applied to the solvent inlet ports simultaneously.

10. The method according to claim 8 wherein the fluid under pressure is a liquid solvent and wherein it is supplied from a separate source for each one of said plurality of the injection valves.

* * * * *